United States Patent [19]
Kim et al.

[11] Patent Number: 5,754,716
[45] Date of Patent: May 19, 1998

[54] OPTICAL MODE MIXER USING FIBER OPTIC BUNDLE

[75] Inventors: James Kim, Mission Viejo; Mark M. Minot, Aliso Viejo, both of Calif.

[73] Assignee: Baxter International Inc., Deerfield, Ill.

[21] Appl. No.: 832,253

[22] Filed: Feb. 7, 1992

[51] Int. Cl.$^6$ .................... G02B 6/26; G02B 6/42
[52] U.S. Cl. .................................... 385/28
[58] Field of Search .................. 385/28, 33–34, 385/1, 24, 43, 124

[56] References Cited

U.S. PATENT DOCUMENTS

| | | | |
|---|---|---|---|
| 3,937,557 | 2/1976 | Milton | 385/33 X |
| 4,229,067 | 10/1980 | Love | 385/28 |
| 4,299,609 | 11/1981 | Aulich et al. | 65/3.13 |
| 4,453,218 | 6/1984 | Sperinde et al. | 364/416 |
| 4,566,753 | 1/1986 | Mannschke | 385/28 X |
| 4,623,248 | 11/1986 | Sperinde | 356/41 |
| 4,669,467 | 6/1987 | Willet et al. | 128/303.1 |
| 4,732,452 | 3/1988 | Carter | 385/33 X |
| 4,817,205 | 3/1989 | Asawa | 385/33 X |
| 4,932,747 | 6/1990 | Russell et al. | 385/117 |
| 4,943,137 | 7/1990 | Speer | 385/26 |
| 4,946,239 | 8/1990 | Garmon | 385/43 |
| 4,973,169 | 11/1990 | Slonecker | 385/1 |
| 5,012,809 | 5/1991 | Shulze | 128/634 |
| 5,016,963 | 5/1991 | Pan | 385/33 |
| 5,050,954 | 9/1991 | Gardner et al. | 385/33 X |
| 5,077,814 | 12/1991 | Shigematsu et al. | 385/28 |
| 5,138,675 | 8/1992 | Schofield | 385/28 |
| 5,181,264 | 1/1993 | Chiaretti et al. | 385/117 X |
| 5,263,110 | 11/1993 | Anderson | 385/117 X |
| 5,267,077 | 11/1993 | Blonder | 385/11 X |
| 5,276,747 | 1/1994 | Pan | 385/34 |
| 5,299,272 | 3/1994 | Buchin | 385/33 X |

FOREIGN PATENT DOCUMENTS

| | | |
|---|---|---|
| A2360895 | 3/1978 | France . |
| 2635486 | 2/1978 | Germany . |
| A3940642 | 6/1991 | Germany . |

OTHER PUBLICATIONS

"Optical Fiber Communications", John M. Senior, Prentice–Hall International, Inc. 1985 p. iii, 184. No Date.
"Mode Mixing in Fiber Optic Oximeter", V. Amirkhanian, W. Lee, *Optical Fibers in Medicine V* SPIE vol. 1201, Jan. 1990, pp. 330–337.
JP 59–224809, *Patent Abstracts of Japan*, vol. 9, No. 101 (P–353) (1824), May 2, 1985 JP.
*SELFOC®Handbook*, NSG America Inc., pp. 84–85, Fig. 4–46.

*Primary Examiner*—Akm E. Ullah
*Attorney, Agent, or Firm*—Bruce Canter; Oppenheimer Poms Smith

[57] ABSTRACT

Improved optical mode mixers for use in conjunction with optical fibers and devices incorporating optical fibers are disclosed and claimed. The optical mode mixers are formed from a coherent, orderly bundle of numerous small diameter optical fibers in a longitudinally aligned, parallel array. The mode mixer is optically linked to the fiber optic cable and effectively reduces undesirable high order modes of light transmission while eliminating alignment sensitivity. The coherent fiber optic bundles may be as short as ten wavelengths of light in length and will have a diameter substantially equal to that of the fiber optic cable to which they are coupled.

25 Claims, 4 Drawing Sheets

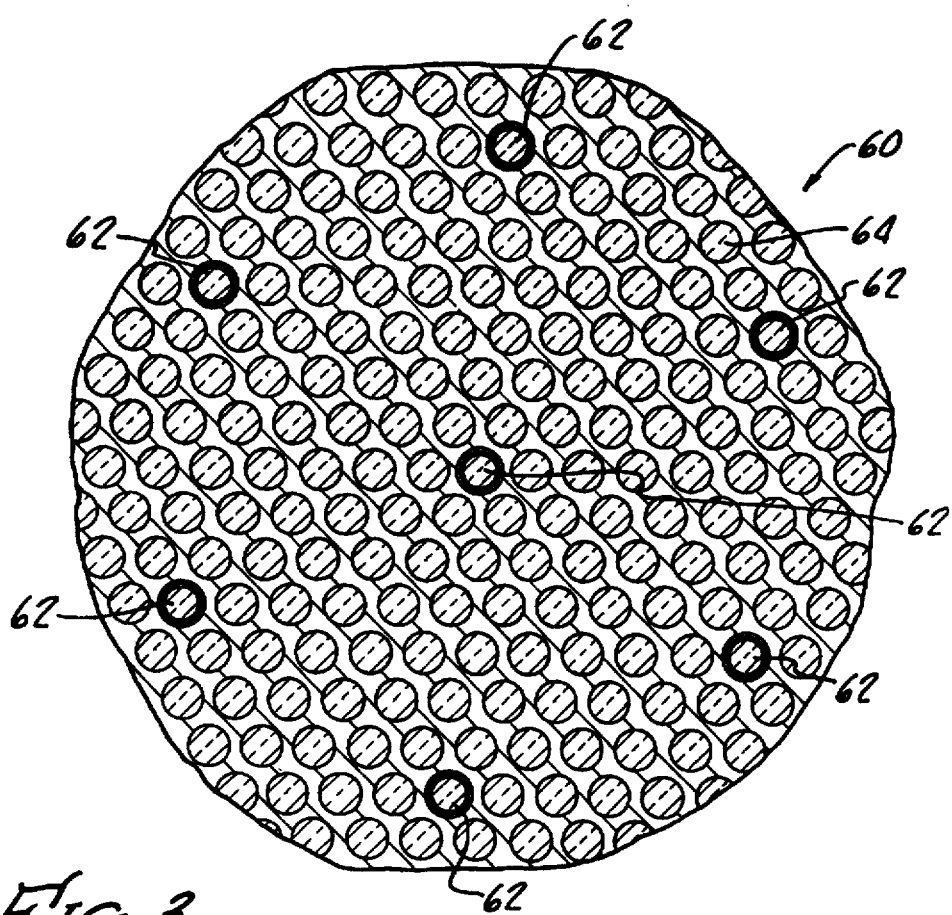
FIG. 3.
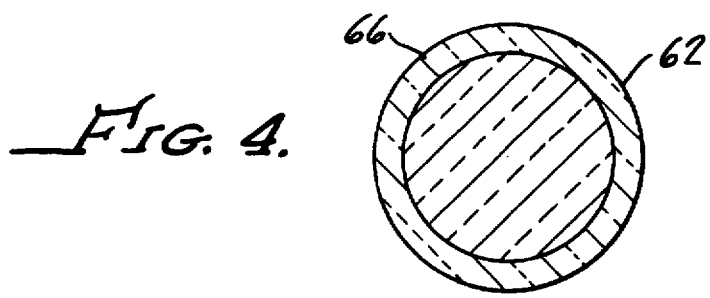
FIG. 4.
FIG. 5.
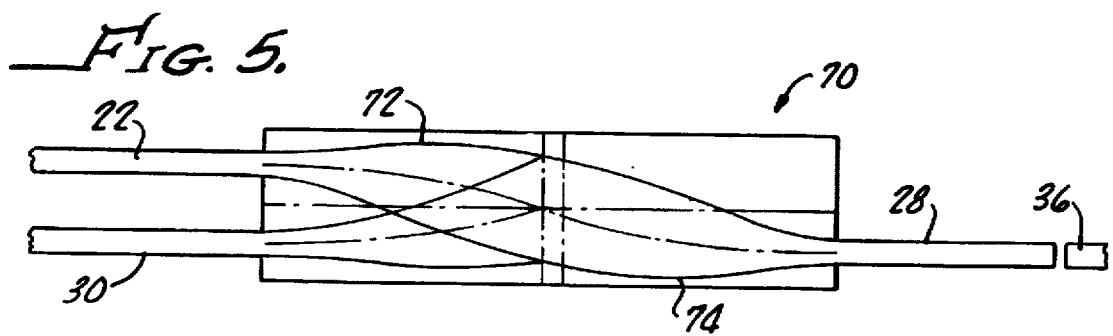

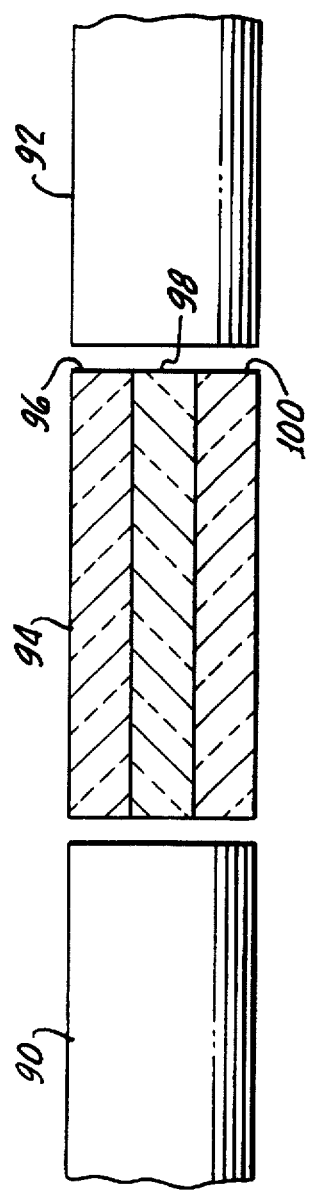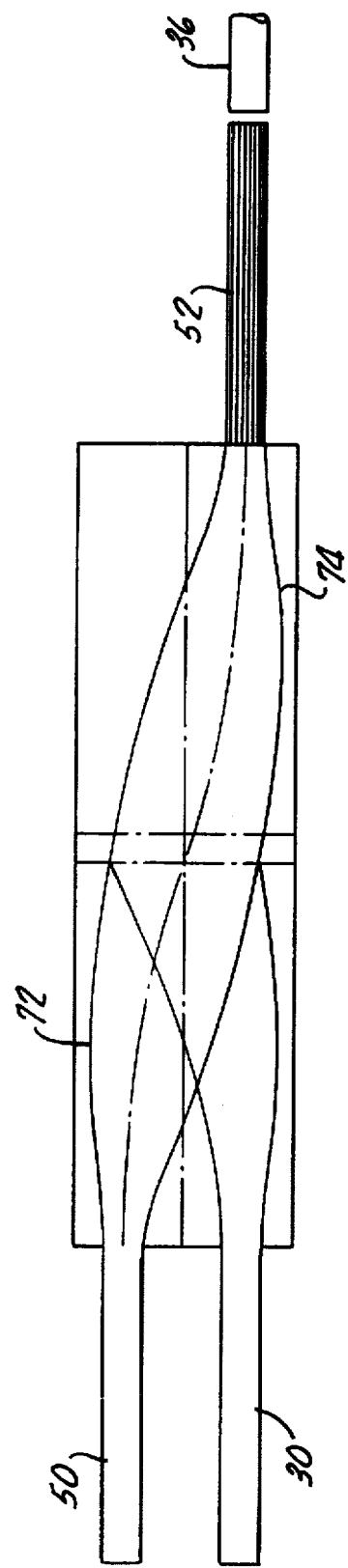

OPTICAL MODE MIXER USING FIBER OPTIC BUNDLE

FIELD OF THE INVENTION

The present invention generally relates to fiber optic light transmission. More particularly, the present invention relates to fiber optic light transmission in which it is desirable to reduce or eliminate high order mode transmission forms.

BACKGROUND OF THE INVENTION

The utilization of light conducting optical fibers to transmit light is well known in the art. The applicability and utilization of fiber optic cables and fibers is presently reaching into virtually every facet of day to day life. Fiber optics are small, flexible, insensitive to electromagnetic fields, and transmit vast quantities of information relative to conventional metallic conductors. As a result, considerable development has been directed toward incorporating fiber optics into a wide variety of systems including telecommunications, computers, and medical devices.

Typically, optical cables are formed of glass or plastic clad cores which themselves are made of glass or plastic have been drawn into relatively uniform, small diameter cables or fibers. The most commonly available in the marketplace are the multimode fibers that will propagate light in a mixture of low and high order modes simultaneously (high and low order modes refer to the angle of propagation of light within the fiber). Single mode fibers are also available for those applications where the modal interference associated with multimode fibers is undesirable.

In some applications fiber composition or geometry and external factors such as microbends or splices may be responsible for increased attenuation of higher order modes of transmission. Additionally, the modal distribution may vary along the length of the fiber due to these internal and external factors.

Accordingly, early practitioners in the art performed accurate transmission measurements on both multimode and single mode fibers in order to compensate for and reduce the influence of external factors on transmission readings. Alternatively, the multimode propagation effects associated with external factors such as light launching conditions, bends or changes in geometry may be accounted for by allowing the mode distribution to reach an equilibrium or steady-state distribution. This distribution generally occurs automatically after propagation has taken place over a certain fiber length depending upon the strength of the mode coupling within the particular fiber. At equilibrium the mode distribution propagates unchanged. As a result, the fiber attenuation and dispersion effects assume consistent or well-defined values.

Unfortunately, in order to reach an equilibrium mode distribution in this manner it may require a fiber several kilometers in length. While this may be suitable for telecommunications requirements, packaging such a length for utilization in space constrained environments is virtually impossible. Accordingly, a number of alternative methods of obtaining an equilibrium modal distribution with shorter fiber lengths have been developed in the art.

For example, modal equilibrium may be achieved using an optical source with a output modal distribution corresponding to the steady state mode distribution of the fiber of interest. This technique may be achieved utilizing an optical arrangement allowing the numerical aperture (a measure of the light gathering power of a fiber similar to the f/number of a lens [NA=½f#]) of the beam to be varied. Thus, by giving the input light beam an angular width equal to the equilibrium distribution numerical aperture of the fiber and adjusting the source spot size on the fiber input face to match the optical power distribution in a cross section of the fiber equilibrium mode equilibrium may be achieved. This is very difficult to achieve in practice.

Alternative mode mixing or mode smoothing techniques quickly induce intermodal coupling within fiber lengths of approximately one meter or less. These generally involve the application of either mechanical perturbations to the fiber, including deformations of the fiber cladding or core, or square or other non-symmetric cross-sectional fiber configurations. Each of these alternatives suffers from one or more disadvantages. For example, it is often difficult to obtain stable, reproducible optical characteristics from either mechanical perturbations or deformations of the fiber. Additionally, in some applications even one meter of fiber is difficult to package and may require coiling into a fiber spool. Additionally, mode mixers based upon sinusoidal or point deformations in the optical fiber cladding and/or core may be unstable over time and are exquisitely sensitive to changes in the amplitude and shape of the deformation. Thus, thermal and mechanical variations may result in nonreproducable transmission characteristics. Mode mixers based upon non-symmetric fiber cross sections are physically compact yet suffer losses incurred in the conversion of the mode field distributions from circularly symmetric to non-symmetric distributions. Moreover, non-symmetrical fibers are difficult and expensive to fabricate.

These problems are particularly well illustrated by consideration of the utilization of fiber optics in medical apparatus due to the physical size constraints inherent in such devices. Medical apparatus and instrumentation have in recent years incorporated the benefits of fiber optic cable where fiber optics have been adapted to illuminate organs and structures internal to the human body without the need for excessive external cutting and tissue trauma. Additionally, arthroscopic surgery and laser treatments using fiber optic cables to transport light have become accepted and common practices. Recently devices utilizing fiber optics to monitor internal body organs and functions before, during and after surgical procedures have been developed. These types of monitoring equipment include oximeters which measure the oxygen content of the blood as it travels throughout the body to monitor cardiac function.

Generally speaking, most modern oximeters utilize a catheter or probe which is inserted into the blood stream through a major artery or vein. The tip of the oximeter probe supplies light through a fiber optic cable. Light reflected from red blood cells is detected through an adjacent fiber optic cable in the probe which is connected to a detector. A saline solution or other anticoagulant solution is emitted from the end of the oximeter in order to prevent coagulation of the blood or clot formation around the working end of the oximeter.

Additional requirements of an oximeter or other apparatus which measures the intensity of reflected light is that a reference must be established so that the intensity of the detected light can be compared with the accurately known intensity of the transmitted light. In order to accomplish this, an optical coupler, or splitter is used. This coupler may be realized using several graded index rod lenses (such as a "SELFOC" lens as manufactured by NSG America, Inc., or the like).

It has been observed that oximeters and other fiber optic apparatus that rely on the intensity of reflected light to generate data perform better when the light emitted is of a particular mode or modal distribution. In many such oximeters, the desired modal distribution of light in the emitting fiber is one which yields a far field optical intensity spatial distribution which is approximately Gaussian and distributed symmetrically about the optical axis of the emitting fiber.

Such a radiation pattern of output light is measured with a far-field scanning apparatus similar to those devices commonly used in the art to measure the numerical aperture of optical fibers.

In order to eliminate undesired modes, the conventional approach in the art is to use a single mode fiber optic cable, or to transmit the optical signal through a multimode fiber optic cable which may be quite long. In either approach, precise alignment of the light source and all intermediate optics is required in order to achieve the proper modal distribution.

Though relatively effective, a number of significant drawbacks are associated with these prior art apparatus. Conveniently packaging a several kilometer long multimode fiber optic cable into a workable device is virtually impossible. As a result, compromises have been made attempting to use shorter coiled fiber optic cables. In addition to these packaging problems, the precise alignment requirements add considerable expense and manufacturing complexity to these devices as highly trained operators are required to repeatedly test and align the delicate fiber optic components. Single mode fiber optic cables may be unsuitable for many uses as it is difficult to couple useful amounts of optical power into them from common optical sources such as LEDs. In addition, they tend to very expensive, and do not tolerate sharp bends in the fiber optic cable.

As noted above, these problems may be common to virtually all apparatus utilizing fiber optic cables to transmit information and are not limited to oximeters and related apparatus.

Accordingly, it would be a significant step forward in the fiber optic cable art if these drawbacks could be economically overcome. Such a development would improve the accuracy and cost effectiveness of fiber optic devices, greatly increasing their utility and applicability. The present invention is such a step forward.

Thus, it is an object of the present invention to provide a mode mixer that effectively attenuates, or eliminates undesired modes of light transmission.

It is a further objection of the present invention to provide a mode mixer that reduces system sensitivity to optical alignment and external factors.

It is an additional object of the present invention to provide a mode mixer which may be rapidly, efficiently, and economically integrated into an optical system and which couples minimal volume.

SUMMARY OF THE INVENTION

These and other objects are achieved by the elegantly simple mode mixer of the present invention which comprises a plurality of small diameter optic fibers longitudinally aligned in parallel, each being smaller in diameter than the diameter of the fiber optic cable used to transport the light beam. The mode mixer of the present invention can be readily incorporated into existing devices and effectively eliminates the need for an extremely long, cumbersome section of fiber optic cable type mode mixer, single mode fiber optic cables nonsymmetric cross-section optical conduits, or sensitive mechanical deformation type mode mixers to remove undesired high order modes of light transmission. As a result, the present invention greatly reduces the sensitivity to alignment of the optical components within the system.

This reduction in sensitivity also reduces the sensitivity of the optical system to mechanical shock, vibration, connector alignment, and thermal changes that could not be tolerated by the devices of prior art. Thus, apparatus incorporating the mode mixer of the present invention are considerably easier and significantly less expensive to manufacture and calibrate, and more robust in operation.

Other features and advantages of the present invention will become apparent from the following detailed description of exemplary embodiments thereof, taken in conjunction with the accompanying drawings, which illustrate, by way of example, the principles of the present invention.

BRIEF DESCRIPTION OF THE DRAWINGS

FIG. 3 is a cross-sectional view of a section of the mode mixer of the present invention taken along plane 3—3 of FIG. 2.

FIG. 4 is a cross-sectional view of an exemplary individual EMA structure.

FIG. 5 is a plan view of a prior art graded index rod lens optical coupler showing the light transfer characteristics thereof.

FIG. 6 is a plan view of a graded index rod lens optical coupler incorporating the mode mixer of the present invention.

FIG. 9 is a cross-sectional view of a fiber optic cable incorporating a mode mixer of the present invention.

DETAILED DESCRIPTION

Though the present invention is widely applicable to virtually all apparatus utilizing fiber optic cable, the features and advantages of the present invention are readily illustrated in the context of an exemplary cardiac catheter oximeter. Accordingly, without limiting the scope of the present invention, the exemplary embodiment of the present invention will be discussed in this context.

Figure 1:
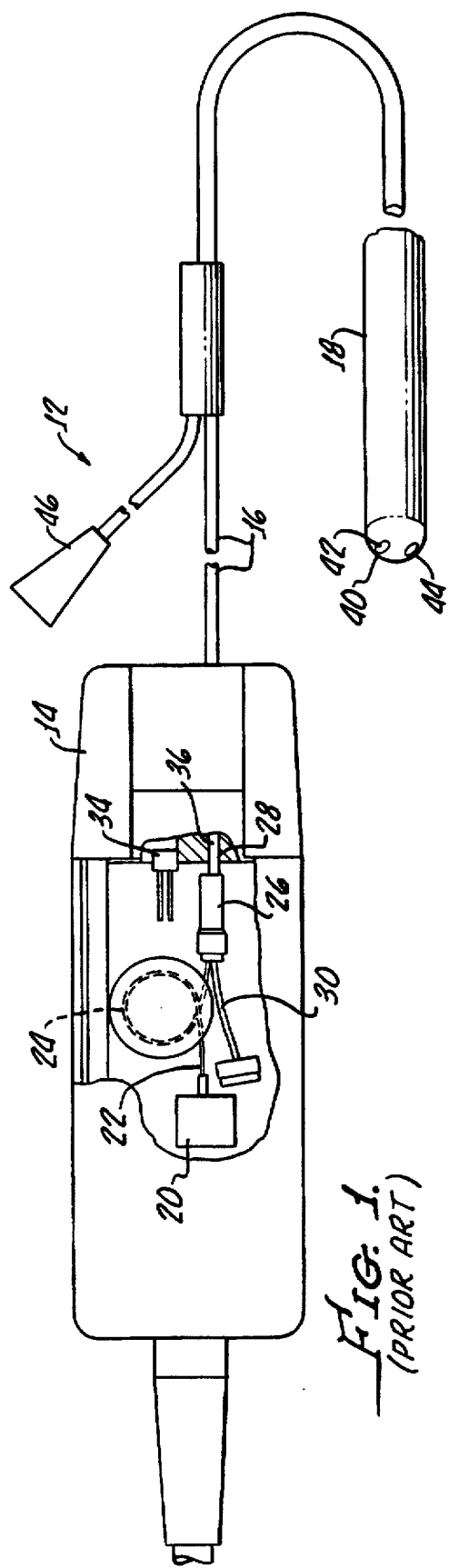
FIG. 1 is a plan view of an exemplary prior art fiber optic cardiac catheter with an integral oximeter.

Referring more particularly to the drawings, FIG. 1 shows an example of a prior art fiber optic cardiac catheter with an integral oximeter generally indicated by reference 12. The device consists of a housing 14 containing a light source 20 which, in the exemplary embodiment, supplies both red and infrared light. Those skilled in the art will appreciate that other characteristic wavelengths of light may be utilized with the present invention as well as single wavelengths. The output light from source 20 is transmitted through optical fiber cable 22 to mode mixer 24. Though optical fiber "cable" typically includes a protective jacketing, for purposes of the present invention cable 22 may or may not be jacketed. Mode mixer 24 is illustrated as a coil of multimode fiber optic cable as discussed above. As those skilled in the art will appreciate, this prior art coil is considerably shorter than the multi-kilometer length necessary to effectively eliminate high order mode light transmissions from the device and is more a compromise to package as much fiber optic cable as possible in the device to decrease high order mode transmission without making the apparatus unwieldy. Nonetheless, mode mixer 24 does attenuate or eliminate high order modes of light transmission, to a limited extent.

High order modes of light are those which reflect at an angle nearly perpendicular to the wall of the fiber optic cable. It is desirable to eliminate these high order mode light transmissions from the device because the presence of uncontrolled high order mode distributions tend to distort the accuracy of the measuring system. Additionally, high order mode distributions are more sensitive to misalignments of optical system components than low-order modes transmissions.

Light exits from mode mixer 24 and is introduced to a graded index rod lens (GRIN Lens) optical coupler 26. Exemplary GRIN Lenses include "SELFOC" lenses such as those manufactured by NSG America, Inc., a subsidiary of Nippon Sheet Glass Company, Ltd. The GRIN Lens optically couples the output light from mode mixer 24 to relay lens 28, and provides reflection of a portion of the light supplied through fiber optic cable 30 to reference detector 32. In this manner, a reference is continuously available. The amplitude of this reference is proportional to the amplitude of the light coming out of mode mixer 24.

Light is coupled through lens 28 into detachable fiber optic cable 36. The light is then conducted through fiber optic cable 40 contained within catheter or cable bundle 16. The light is conveyed to distal catheter end 18 where it is emitted into the blood stream through the end of fiber optic cable 40. Reflected light is then conveyed back through a separate fiber optic cable 42 within cable bundle 16, to light detector 34 which is located in housing 14.

The underlying principle of the fiber optic oximeter is that light of selected wavelengths is transmitted through one of the multimode optical fibers within the catheter bundle (fiber optic cable 40 in FIG. 1) to the blood flowing past the catheter tip 18. The light is absorbed by the hemoglobin constituents of the blood and is also scattered by blood cells. The reflected light is then transmitted back to the second optical fiber, fiber optic cable 42, to the photodetector 34. Because oxyhemoglobin and hemoglobin absorb light differently at the selected wavelengths, the reflected light can be analyzed to determine oxygen saturation.

In the exemplary embodiment of the present invention light source 20 contains both red LED (660 nanometer) and IR LED (800 nanometer) light launched into the core of a 500 micrometer diameter PMMA type plastic optical fiber through a dichroic beam splitter and microball lens (not shown) as known in the art. The plastic fiber optic cable has an exemplary numerical aperture of 0.47 and thus will collect all of the IR beam and will strip the high numerical aperture light of the red LED. The coiled fiber on mode mixer 24 is approximately 20 cm long and produces an output beam with an overlap of red light and IR light close to 65%. In order to achieve the necessary overlap of 95% or better the IR light needs to be expanded and the high numerical aperture (high order mode) portion of the red light needs to be stripped out. This is accomplished with prior art by looping the fiber of mode mixer 24 into a small bend radius (0.5 inch diameter) in several turns.

The final device used to limit the numerical aperture of both the red and IR light is the GRIN Lens 26 which acts as a one-to-one imager. The resultant output will have numerical aperture overlaps ranging from 92% to 100% and, when the output beam is coupled into catheter fiber 40, the far-field scan of red and IR light from catheter tip 18 shows and acceptable overlap as illustrated by the far-field radiation scan of FIG. 7.

Those skilled in the art will appreciate that the overlap between the two wavelengths of light is not perfect and the pattern shows a dip at its peak. Thus, the accuracy of the prior art oximeter may be less than desirable and, more importantly, is extremely sensitive to component alignment within the oximeter. As known in the art, an optical module with a low overlap will have a different coupling efficiency for different light. This difference will vary depending upon the medium surrounding the catheter tip. Therefore, good overlap in the optical module is essential to the accuracy of the oximeter.

The critical parameters for achieving acceptable overlap in such prior art devices include not only the material properties but the position and alignment of the various optical components. This results in significant manufacturing costs and decreased reproducability or operational stability over time as highly skilled operators are needed to calibrate and adjust each instrument. Nonetheless, in spite of these drawbacks the prior art apparatus have proven generally successful, though expensive.

In this illustrative embodiment the amount of oxygen in the blood is determined by the ratio of the red and infrared signal supplied by light source 20 and measured by reference detector 32 and reflected light detector 34. The measured information is then electronically transmitted to a processor (not shown) whose output is expressed in terms of percent oxygen saturation.

Opening 44 in catheter end 18 provides a means for injection of saline or an anti-clotting agent to prevent clotting on the end of catheter tip 18 interfering with the operation of the catheter. The fluid which exits through opening 44 is introduced through opening 46. Various drugs also may be introduced in this manner.

Figure 7:
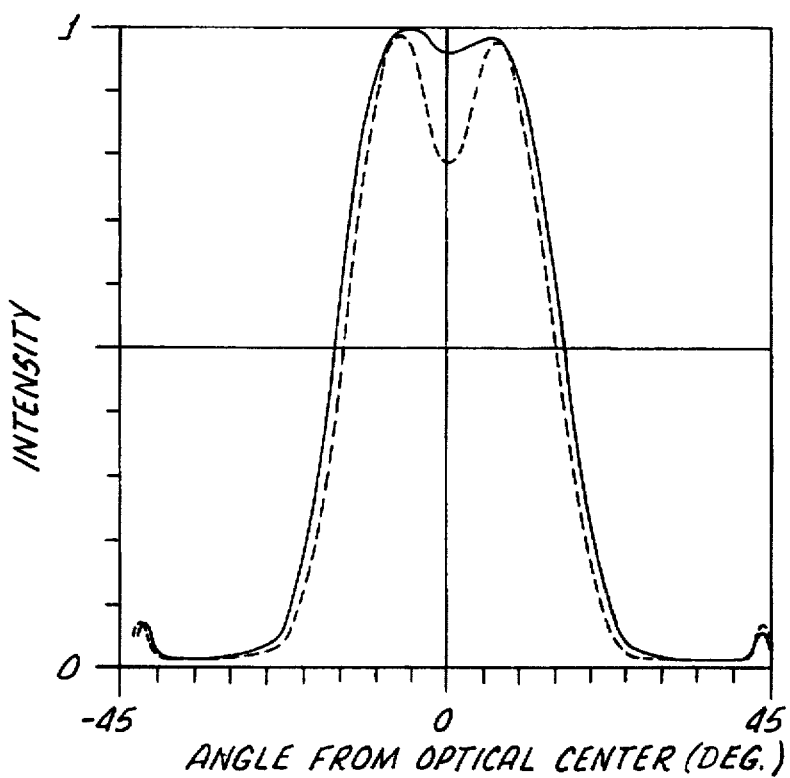
FIG. 7 is a plot of the far field radiation scan of the light emission intensity of prior art devices showing intensity as a function of light exit angle with respect to a fiber optic cable propagating two different wavelengths of light.

As noted above, the components of the prior art device as shown is FIG. 1 must be carefully aligned to avoid producing an undesirable, low overlap light modal distribution as shown in FIG. 7. Fine tuning adjustments are made to precisely align each of the optical elements, including the positioning of each element, as well as the tension applied to fiber optic cables 22 and 30 and how tightly wrapped the fiber optic cable is in mode mixer 24 as the intensity is sensitive to all of those factors.

Figure 2:
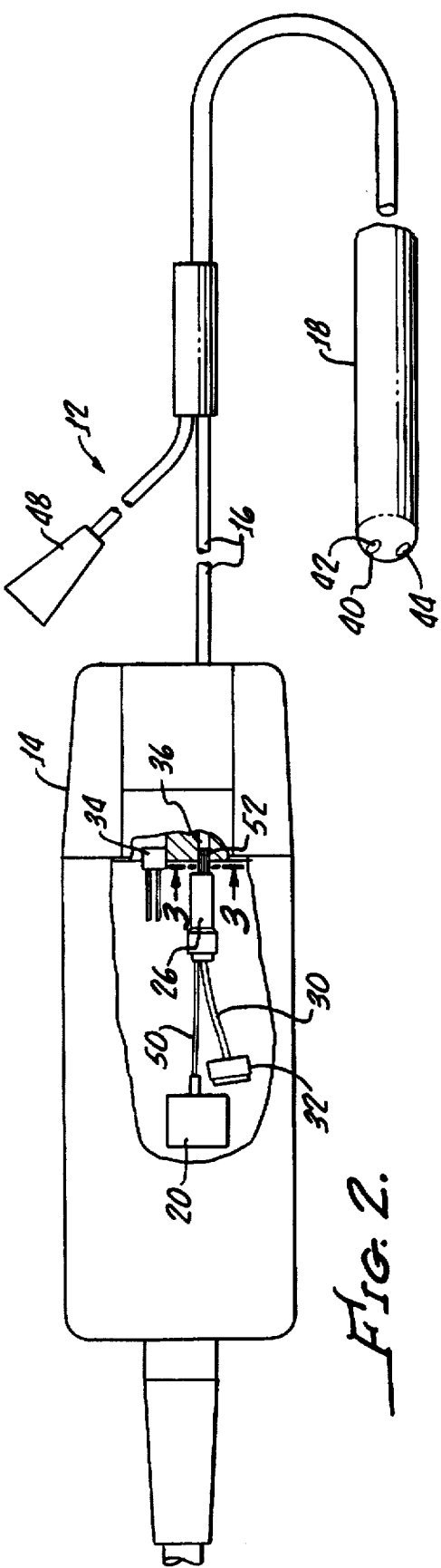
FIG. 2 is a plan view of a fiber optic cardiac catheter with an integral oximeter utilizing the mode mixer of the present invention.

In contrast, as illustrated in FIG. 2, the present invention uses a fiber optic cable 50 to convey output light from light source 20 to the GRIN Lens assembly in housing 26 and the output of the GRIN Lens assembly is then transferred through mode mixer 52 which attenuates or eliminates undesirable high order modes of light transmittal. Thus, the bulky coil of prior art mode mixer 24 and the associated packaging and alignment problems can be eliminated from the device, if desired. Light exits mode mixer 52 and is conveyed through fiber optic cable 36 in detachable cable bundle or catheter 16 to catheter end 18 in a conventional manner as with the prior art device.

Mode mixer 52 is formed of a plurality of relatively small diameter optical fibers oriented in parallel to one another. An exemplary cross section 60 of the plurality of optical fibers 64 is shown in FIG. 3. The exemplary cross section 60 includes a number of optional extra mural absorption (EMA) structures 62. EMA structures 62 function to eliminate stray light or crosstalk between fibers. In the present invention, these EMA structures assist in attenuating or eliminating high order modes of light transmissions but are not essential to the practice of the invention. These EMA structures can be in the form of a painting or coating on each fiber such as the layer of black glass 66 as shown in FIG. 4. Alternative EMA structures may be produced by placing small amounts of black glass or plastic in the interstices around each fiber in the bundle or in the form of the statistical EMA structures as represented by reference numerals 62 in which several transmitting fibers have been replaced with black fibers.

The diameter of the individual fibers 64 and 62 within the exemplary mode mixer bundle 52 may very widely as long as the diameter of each individual small diameter optical fiber is less than that of the fiber optic cable optically coupled to the mode mixer. Though it is contemplated as being within the scope of the present invention to utilize fibers each having identical diameters ranging from approximately 3 microns to 60 microns or more, it is preferred that the coherent fiber optic bundle mode mixer of the present invention be formed from a plurality of readily available, low cost standard fiber sizes ranging from approximately 6 to 8 microns. The diameter of the exemplary fiber optic cable 36 which transports light to catheter 18 is approximately 250 microns in diameter. Thus, there are approximately 10,000 6-8 micron diameter fibers in the exemplary mode mixer 52 which feed light from the GRIN Lens to the fiber optic cable 36.

The length of the mode mixer 52 is approximately ¼ inch in this exemplary embodiment. It is recognized that a longer or shorter mode mixer can be used within the scope of the present invention. It is believed that a mode mixer which is longer than approximately 10 wavelengths of the light being transmitted should successfully attenuate or eliminate undesired high order mode transmissions. The exact number of wavelengths which will sufficiently attenuate high order mode transmissions is uncertain; however, favorable results should be obtained in most cases with a length of less than ¼ inch. In the commercial environment in which the present invention operates it is desirable to use components of sufficiently large size so that they can be assembled by hand, if necessary, and their orientation adequately observed and secured by an operator or technician. Thus, mode mixers smaller then ¼ inch in length may be difficult to handle and assemble. The mode mixer itself can be fabricated utilizing conventional fiber optic materials and techniques including those developed for the production of fiber optic faceplates such as those available from Incom, Inc. of Southbridge, Mass.

Figure 8:
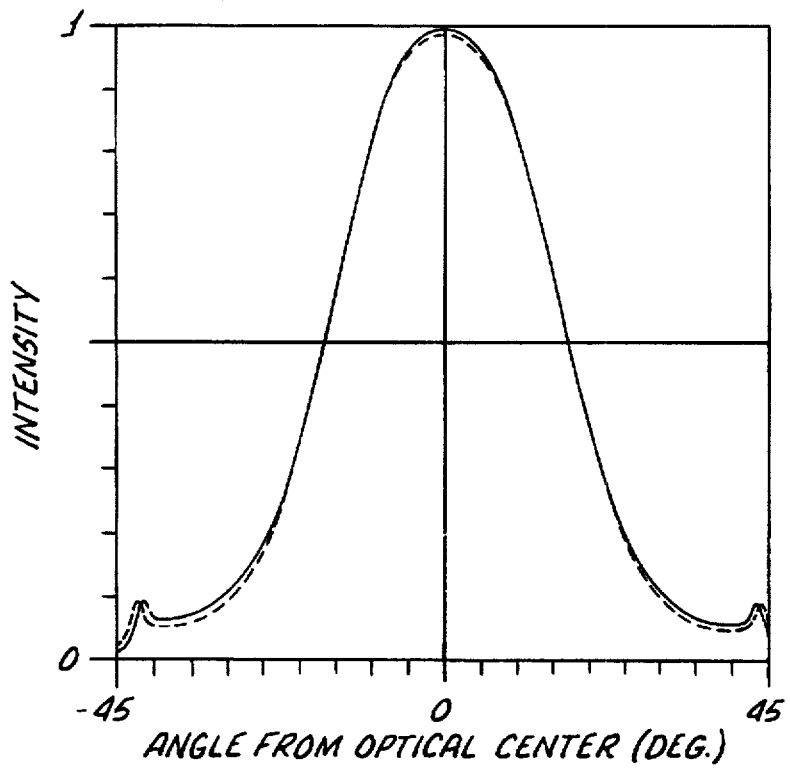
FIG. 8 is a plot of the far field radiation scan of the light emission intensity of the present invention showing intensity as a function of light exit angle with respect to a fiber optic cable propagating two different wavelengths of light.

The effectiveness of the mode mixer of the present invention is best illustrated in the comparative far-field radiation scan light emission intensity plots of FIGS. 7 and 8. Referring first to FIG. 7, which illustrates the far-field intensity profile of light from two optical sources, red light generally represented by a solid line, and IR light represented by a dashed line. It is apparent in FIG. 7 that the prior art mode mixer produces a spatial separation of light from the two optical sources as well as a significant drop off in intensity at a 45° angle. In contrast, the mode mixer of the present invention produces a smooth almost Gaussian distribution of light intensity with minimal differences between the two transmitted light signals and no peak drop off as shown in FIG. 8. This greatly increases both the accuracy and the reproducability of the oximeter utilizing the present invention. As a result, the present invention produces an oximeter that is simple and economical to manufacture, calibrate, and use.

Attachment of the mode mixer to the GRIN lenses is shown in FIG. 6. In the prior art embodiment of FIG. 5, GRIN Lens 70 consists of two elements 72 and 74 of approximately equal length. Input element 72 has light coupled into the optical cavity of element 72 through fiber optic cable 22 which corresponds to the output of mode mixer 24 shown in FIG. 1. Once the light has entered the optical cavity of element 72, part of the light is reflected back to fiber optic cable 30 which conveys the reflected light to reference detector 32 as shown in FIGS. 1 and 2. There is a gap between optical element 72 and optical element 74 of approximately 0.003 inch which may be occupied by a material having a different refractive index from that of optical elements 72 and 74. Light is directly coupled from optical element 72 to optical element 74 through this gap. This light is conveyed to optical element 28 which, in the prior art, is a simple lens which focuses the transmitted light into fiber optic cable 36. This creates a series of three lens elements 72, 74 and 28 referred to as a trilens arrangement.

In contrast, as shown in FIG. 6, a GRIN Lens illustrating the features of the present invention incorporates a fiber optic bundle mode mixer 52 in place of the simple output lens 28 of the prior art. As with the prior art embodiment, mode mixer 52 is preferably bonded to optical element 74 with optical cement such as Epotek 301 and the output of the fiber optic bundle is conveyed to fiber optic cable 36 through an air gap which is approximately 0.003 inches wide.

Accordingly, it is readily apparent that the mode mixer of the present invention is a simple substitution for existing prior art optical elements yet eliminates the need for single mode fibers or lengthy and awkward multimode fiber optic attenuators. Moreover, in the prior art GRIN Lens the placement of lens 28 against optical element 74 could affect the performance of the device. More specifically, lens 28 had to be substantially centered about the output focal point of optical element 74. As a result, this lead to difficulties in manufacture and a large number of rejected device. In contrast, the fiber optic bundle mode mixer of the present invention is less sensitive to placement against optical element 74. Moreover, incorporating the fiber optic mode mixer of the present invention significantly reduces the sensitivity of the device to light launching conditions or optical component alignment imperfections. Thus, manufacture of the device is considerably easier and less expensive. Further, by eliminating the need for the prior art mode mixer 24 and its associated alignment problems the manufacture and adjustment of the device is simplified even more. As an added benefit, the elimination of additional elements and critical adjustment problems enhances the utility and operability of these devices by eliminating their sensitivity to shocks, thermal expansion, and abuse. This improves the reliability and service life of the devices.

It should also be noted that the mode mixers of the present invention can be utilized without eliminating prior art components such as mode mixer 24 in FIG. 1. Though the prior art mode mixer may be a redundant feature, the utilization of the present invention does not require a complete redesign of the device as it can be retrofitted to existing designs with minimal modification.

As noted above, the mode mixer of the present invention is also readily applicable to a wide variety of fiber optic devices. For example, as shown in FIG. 9, the present invention can be applied to fiber optic transmission lines by inserting a fiber optic bundle mode mixer 94 between fiber optic cables 90 and 92 (which may or may not be jacketed). The diameter of fiber optic cable 90 need not be identical to the diameter of fiber optic cable 92; however, fiber optic mode mixer 94 is formed of one or more optical fibers 96, 98 and 100, each with a diameter that is smaller than either the diameter of fiber optic cable 90 or of fiber optic cable 92.

Fiber optic mode mixer 94 also may contain EMA structures (not shown) to further attenuate or eliminate high order modes of light transmission. The diameter of each of the smaller diameter fibers of fiber optic mode mixer 94 is sufficiently less than the diameters of cables 90 and 92 to enable fiber optic mode mixer 94 to attenuate or eliminate high order modes of light transmission. For example, in one embodiment, fiber optic cable 90 has a diameter of 250 microns, as does fiber optic cable 92. Fiber optic mode mixer 94 has a similar diameter and is provided with a plurality of small diameter optical fibers each having a diameter of 6 to 8 microns. The plurality of fibers within fiber optic mode mixer 94 may be arranged as shown in FIG. 3 resulting in approximately 10,000 fibers comprising fiber optic mode mixer 94.

In closing, it is to be understood that the embodiments of the invention disclosed herein are illustrative of the principles of the invention. Other modifications may be employed which are within the scope of the invention and thus, the present invention is not limited to utilization in conjunction with cardiac catheters or oximeters. Accordingly, the present invention is not limited to that precisely as shown and described in the present specification.

What is claimed is:

1. An optical mode mixer for use in conjunction with a fiber optic cable transmitting light of at least one characteristic wavelength, said mode mixer comprising:

a spatially coherent fiber optic bundle optically linked in light conducting communication to said fiber optic cable and formed of a plurality of longitudinally disposed, coaxial, small, optical fibers each having a uniform diameter of about 3 microns to 60 microns.

2. The optical mode mixer of claim 1 wherein said plurality of longitudinally disposed, generally parallel, small diameter optical fibers are arranged in an orderly pattern.

3. The optical mode mixer of claim 2 wherein said orderly pattern is a close-packed grid.

4. The optical mode mixer of claim 1 further comprising a plurality of extramural absorption structures.

5. The optical mode mixer of claim 1 wherein each of said plurality of longitudinally disposed, generally parallel, small diameter optical fibers has a diameter from about 3 microns to 10 microns.

6. The optical mode mixer of claim 1 wherein said coherent fiber optic bundle comprises at least three longitudinally disposed, generally parallel, small diameter optical fibers.

7. The optical mode mixer of claim 1 wherein said coherent fiber optic bundle comprises at least 1000 longitudinally disposed, generally parallel, small diameter optical fibers.

8. The optical mode mixer of claim 1 wherein said coherent fiber optic bundle has a length equal to a whole number multiple of said characteristic wavelength.

9. The optical mode mixer of claim 8 wherein said whole number multiple is at least 10.

10. The optical mode mixer of claim 1 wherein said coherent fiber optic bundle is optically linked in light conducting communication to said fiber optic cable by an adhesive bond.

11. A method for altering the mode distribution of light transmitted through a fiber optic cable, said method comprising the steps of:

providing an optical mode mixer formed of a spatially coherent bundle of at least three longitudinally disposed, coaxial, small, uniform diameter optical fibers; and optically linking said optical mode mixer in light conducting communication with said fiber optic cable.

12. The method of claim 11 wherein each of said small diameter optical fibers has a diameter from about 3 microns to 60 microns.

13. The method of claim 11 wherein said optically linking step further comprises forming a light conducting adhesive bond between said optical mode mixer and said fiber optic cable.

14. A low cost, high efficiency catheter based fiber optic oximeter comprising:

at least one light source for generating a light output having a characteristic wavelength;

said light source optically connected to a means for splitting said light output into a transmitted output and a reference output;

means for detecting said reference output optically connected to said means for splitting said light output;

a coherent fiber optic bundle optical mode mixer for altering the mode distribution and removing higher order modes of light from said light output, said optical mode mixer formed of a plurality of longitudinally disposed, coaxial, small diameter optical fibers and optically connected to said means for splitting said light output; and means for transmitting said light output from said optical mode mixer to a fiber optic cardiac catheter.

15. The fiber optic oximeter of claim 14 wherein said plurality of longitudinally disposed, generally parallel, small diameter optical fibers forming said optical mode mixer are arranged in an orderly pattern.

16. The fiber optic oximeter of claim 15 wherein said orderly pattern is a close-packed grid.

17. The fiber optic oximeter of claim 14 wherein said fiber optic bundle optical mode mixer further comprises a plurality of extramural absorption structures.

18. The fiber optic oximeter of claim 14 wherein each of said plurality of longitudinally disposed, generally parallel, small diameter optical fibers has a diameter from about 3 microns to 60 microns.

19. The fiber optic oximeter of claim 14 wherein said coherent fiber optic bundle optical mode mixer comprises at least 3 longitudinally disposed, generally parallel, small diameter optical fibers.

20. The fiber optic oximeter of claim 14 wherein said coherent fiber optic bundle optical mode mixer has a length equal to at least 10 of said characteristic wavelengths of said light output.

21. An optical mode mixer for use in conjunction with a fiber optic cable transmitting light of at least one characteristic wavelength, said mode mixer comprising:

a spatially coherent fiber optic bundle optically linked in light conducting communication to said fiber optic cable and formed of a plurality of longitudinally disposed, coaxial, small, uniform diameter optical fibers each having a uniform diameter of about 3 microns to 10 microns.

22. An optical mode mixer for use in conjunction with a fiber optic cable transmitting light of at least one characteristic wavelength, said mode mixer comprising:

a spatially coherent fiber optic bundle optically linked in light conducting communication to said fiber optic cable and formed of at least three longitudinally disposed, coaxial, small, uniform diameter optical fibers.

23. An optical mode mixer for use in conjunction with a fiber optic cable transmitting light of at least one characteristic wavelength, said mode mixer comprising:

a spatially coherent fiber optic bundle optically linked in light conducting communication to said fiber optic cable and formed of at least one thousand longitudinally disposed, coaxial, small, uniform diameter optical fibers.

24. A method for altering the mode distribution of light transmitted through a fiber optic cable, said method comprising the steps of:

providing an optical mode mixer formed of a spatially coherent bundle of a plurality of longitudinally disposed, coaxial, small, optical fibers each having a uniform diameter of about 3 microns to 60 microns; and optically linking said optical mode mixer in light conducting communication with said fiber optic cable.

25. A method for altering the mode distribution of light transmitted through a fiber optic cable, said method comprising the steps of:

providing an optical mode mixer formed of a spatially coherent bundle of a plurality of longitudinally disposed, coaxial, small, uniform diameter optical fibers; and optically linking said optical mode mixer in light conducting communication with said fiber optic cable by forming a light conducting adhesive bond between said optical mode mixer and said fiber optic cable.

* * * * *